(12) United States Patent
Clemente et al.

(10) Patent No.: US 8,025,868 B2
(45) Date of Patent: *Sep. 27, 2011

(54) COMPOSITIONS COMPRISING AN ULTRAVIOLET RADIATION-ABSORBING POLYMER

(75) Inventors: Rudy Clemente, Belle Mead, NJ (US); Curtis Cole, Ringoes, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 65 days.

This patent is subject to a terminal disclaimer.

(21) Appl. No.: 12/535,299

(22) Filed: Aug. 4, 2009

(65) Prior Publication Data

US 2009/0324523 A1 Dec. 31, 2009

Related U.S. Application Data

(63) Continuation of application No. 12/491,064, filed on Jun. 24, 2009.

(60) Provisional application No. 61/076,927, filed on Jun. 30, 2008.

(51) Int. Cl.
   *A61K 8/00* (2006.01)
   *A61K 8/18* (2006.01)
   *A61K 31/74* (2006.01)
   *A61K 8/02* (2006.01)
   *A61K 33/42* (2006.01)
   *A61Q 17/04* (2006.01)
   *A01N 59/26* (2006.01)

(52) U.S. Cl. ......... 424/60; 424/59; 424/78.03; 424/401; 424/601; 424/604; 514/937

(58) Field of Classification Search .................... 424/59, 424/60, 78.03, 401, 601, 604; 514/937
   See application file for complete search history.

(56) References Cited

U.S. PATENT DOCUMENTS

| | | | |
|---|---|---|---|
| 4,107,290 A | 8/1978 | Jacquet et al. |
| 4,489,057 A | 12/1984 | Welters et al. |
| 4,524,061 A | 6/1985 | Cho et al. |
| 4,528,311 A | 7/1985 | Beard et al. |
| 4,611,061 A | 9/1986 | Beard et al. |
| 4,919,934 A | 4/1990 | Deckner et al. |
| 5,063,048 A | 11/1991 | Saitoh et al. |
| 5,243,021 A | 9/1993 | Langer et al. |
| 5,372,804 A | 12/1994 | Khoshdel et al. |
| 5,403,944 A | 4/1995 | Frater et al. |
| 5,487,885 A | 1/1996 | Sovak et al. |
| 5,565,531 A | 10/1996 | Blank |
| 5,714,134 A | 2/1998 | Richard et al. |
| 5,741,924 A | 4/1998 | Sovak et al. |
| 5,776,439 A | 7/1998 | Raspanti et al. |
| 5,783,173 A | 7/1998 | Bonda et al. |
| 5,869,030 A | 2/1999 | Dümler et al. |
| 5,993,789 A | 11/1999 | Bonda et al. |
| 6,018,044 A | 1/2000 | Huber |
| 6,123,928 A | 9/2000 | Sovak et al. |
| 6,193,959 B1 | 2/2001 | Bernasconi et al. |
| 6,338,838 B1 | 1/2002 | Berset et al. |
| 6,376,679 B2 | 4/2002 | Leduc et al. |
| 6,800,274 B2 | 10/2004 | Bonda et al. |
| 6,899,866 B2 | 5/2005 | Bonda |
| 6,962,692 B2 | 11/2005 | Bonda et al. |
| 2004/0028626 A1 * | 2/2004 | Candau .......................... 424/59 |
| 2005/0186154 A1 | 8/2005 | Bonda et al. |
| 2007/0098653 A1 | 5/2007 | Tamasawa et al. |
| 2009/0098367 A1 | 4/2009 | Wenzel et al. |

FOREIGN PATENT DOCUMENTS

| | | |
|---|---|---|
| EP | 0 273 202 A | 7/1988 |
| EP | 0 897 716 A | 2/1999 |
| EP | 0 897 716 B | 2/1999 |
| FR | 2818143 A | 6/2002 |
| FR | 2892633 A | 5/2007 |
| JP | 09239311 A | 9/1997 |
| JP | 10316726 A | 12/1998 |
| JP | 11001420 A | 1/1999 |
| JP | 2004-292555 A | 10/2004 |
| WO | WO 90/03809 A | 4/1990 |
| WO | WO 93/04665 A | 3/1993 |
| WO | WO 01/08647 A | 2/2001 |

OTHER PUBLICATIONS

Steward et al, "Catalytic Chain Transfer Polymerisation of Functional Methacrylates", internet article [Online] 1998, pp. 1-11. URL: <http://www.warwick.ac.uk/fac/sci/Chemistry/polymers/downloads/stewardascm1998.pdf> [retrieved on Oct. 29, 2009].

Aultz, "The Development of a Polymerisable Benzotriazole Stabilise", *Speciality Chemicals* (1996) vol. 16, No. 2, pp. 71-74.

Bonda et al., Cosmetic & Toiletries Magazine (2002) vol. 115, No. 6, pp. 37-45.

Janssen Pharmaceutica, Material Safety Data Sheet, NORBLOC® 6000 (Apr. 1997).

Janssen Pharmaceutica, Material Safety Data Sheet, NORBLOC® 7966 (Apr. 1997).

* cited by examiner

*Primary Examiner* — Johann Richter
*Assistant Examiner* — Luke Karpinski

(57) ABSTRACT

Ultraviolet radiation-absorbing polymers having a first pendant group that comprises an ultraviolet radiation-absorbing moiety and a second pendant group that comprises at least one siloxane linkage and/or an intermediate length carbon chain are disclosed. Personal care compositions including the ultraviolet radiation-absorbing polymer are provided.

11 Claims, 1 Drawing Sheet

COMPOSITIONS COMPRISING AN ULTRAVIOLET RADIATION-ABSORBING POLYMER

CROSS-REFERENCE TO RELATED APPLICATIONS

This application is a continuation of U.S. application Ser. No. 12/491,064, filed on Jun. 24, 2009, which claims the benefit of U.S. provisional application 61/076,927, filed on Jun. 30, 2008, the complete disclosures of which are hereby incorporated herein by reference for all purposes.

FIELD OF THE INVENTION

The present invention relates to improved sunscreen compounds and topically-acceptable compositions that include these sunscreen compounds.

BACKGROUND OF THE INVENTION

The prolonged exposure to UV radiation, such as from the sun, can lead to the formation of light dermatoses and erythemas, as well as increase the risk of skin cancers, such as melanoma, and accelerate skin aging, such as loss of skin elasticity and wrinkling.

Numerous sunscreen compounds are commercially available with varying ability to shield the body from ultraviolet light. For example, the various sunscreen compounds may absorb or block ultraviolet different portions of the ultraviolet spectrum, such as ultraviolet light having wavelengths in both the UV-A range (from about 320 to 400 nm) and the UV-B range (from about 280 to about 320 nm), or some combination of both of these spectral ranges.

It has been suggested to use sunscreen molecules having high molecular weights in order to reduce the penetration of the sunscreen molecule through the epidermis. However, only a limited number of options for high molecular weight sunscreen compounds exist. As such, applicants have recognized it would desirable to have new polymeric sunscreen compounds (ultraviolet radiation-absorbing polymers) that are suitable for inclusion in topical sunscreen compositions. It would also be desirable for the UV-absorbing polymers to, when formulated, provide compositions that are capable of imparting one or more of good spreadibility, low gloss, non-greasy texture, waterproofing, high SPF, high PFA, and favorable PFA/SPF ratio (broad spectrum protection). Applicants have discovered that UV-absorbing polymers comprising a first pendant group that comprises a UV-absorbing moiety and a second pendant group that comprises at least one siloxane linkage and/or an intermediate length carbon chain provide particular advantages, whether used alone or blended with other UV-absorbing polymers.

SUMMARY OF THE INVENTION

In one aspect, the invention features a UV-absorbing polymer having the following chemical structure:

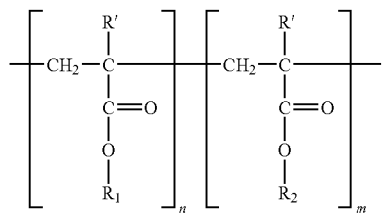

wherein $R_1$ is a first pendant group that comprises a UV-absorbing moiety, such as a UV-A absorbing moiety, preferably a UV-absorbing triazole; $R_2$ is a second pendant group that comprises: a) at least one, such as 1 to about 50, siloxane linkages, b) a saturated or unsaturated hydrocarbon moiety having an intermediate number of carbon atoms, such as 7 to 16 carbon atoms, or c) a combination thereof; each R' is independently H or $C_1$ to $C_{12}$ alkyl; n is 1 to 6000; and m is 2 to 6300. In one embodiment, the UV-absorbing polymer has a weight average molecular weight of at least about 2000 and comprises at least about 5 mole % of $R_1$. In another embodiment, $R_2$ is free of UV-absorbing moieties.

In another aspect, the invention features an aqueous composition comprising water and a UV-absorbing polymer having the following chemical structure:

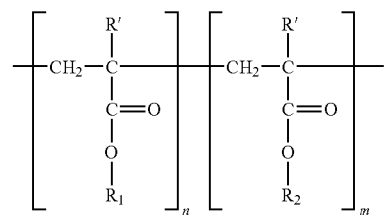

wherein $R_1$ is a first pendant group that comprises a UV-absorbing moiety, such as a UV-A absorbing moiety, preferably a UV-absorbing triazole; $R_2$ is a second pendant group that comprises: a) at least one, such as 1 to about 50 siloxane linkages, b) a saturated or unsaturated hydrocarbon moiety having an intermediate number of carbon atoms, such as 7 to 16 carbon atoms, or c) a combination thereof; each R' is independently H or $C_1$ to $C_{12}$ alkyl; n is 1 to 6000; and m is 2 to 6300. In one embodiment, the UV-absorbing polymer has a weight average molecular weight of at least about 2000 and comprises at least about 5 mole % of $R_1$. In another embodiment, $R_2$ is free of UV-absorbing moieties.

In another aspect, the invention relates to method of protecting mammalian skin or hair from UV radiation comprising topically applying to the skin or hair the UV-absorbing polymer of the invention.

In another aspect, the invention features a composition that comprises a first UV-absorbing polymer that includes a UV-A absorbing moiety and a second UV-absorbing polymer that includes a UV-B absorbing moiety. The blend is capable of providing both synergistic SPF and synergistic PFA protection over a mass percent range of the two polymers of at least about 40%.

In another aspect, the invention features a composition comprising a first UV-absorbing polymer that includes a UV-A absorbing moiety; and a second UV-absorbing polymer that includes a UV-B absorbing moiety, wherein the first UV-absorbing polymer has a PFA/SPF ratio greater than 0.3 and the second UV-absorbing polymer has a UV-B absorber has a PFA/SPF ratio less than 0.3.

In another aspect, the invention features a composition comprising: 1) a first UV-absorbing polymer having a carbon chain (C—C) backbone and that includes a UV-A absorbing moiety; and 2) a second UV-absorbing polymer having a siloxane backbone and that includes a UV-B absorbing moiety.

In another aspect, the invention features a composition that comprises: 1) a first UV-absorbing polymer having an C—C backbone, a first pendant group that includes a first UV-absorbing moiety and a second pendant group comprising at least one siloxane group, wherein the second pendant group is free of UV-absorbing moieties; and 2) a second UV-absorbing polymer that includes at least one siloxane and a second UV absorbing moiety.

DETAILED DESCRIPTION OF THE INVENTION

Figure 1:
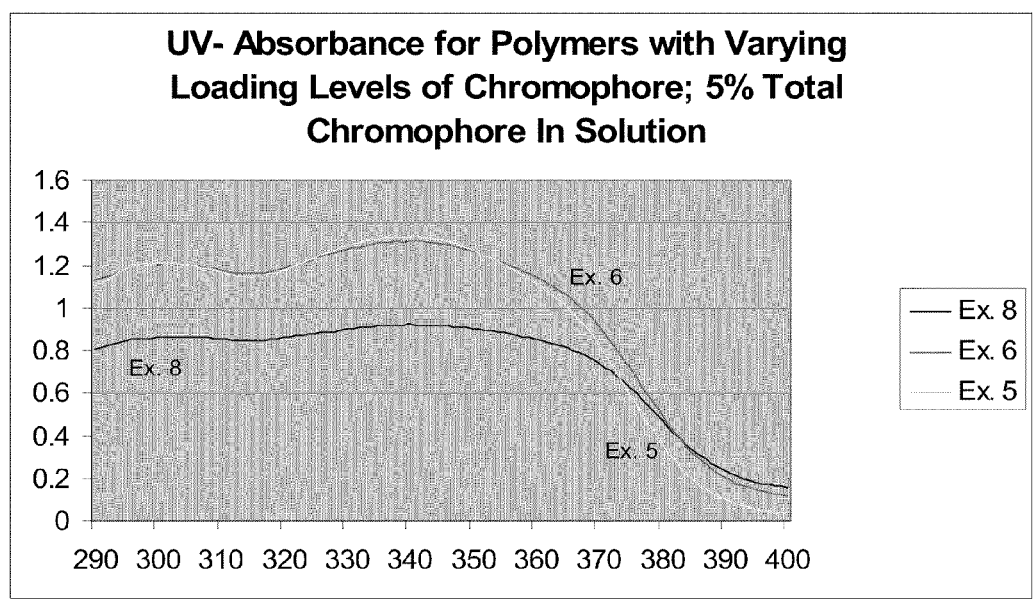
FIG. 1 shows the absorbance spectra for the UV-absorbing polymers of Examples 5 and 6 and the homopolymer of Example 8.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, unless otherwise indicated, all alkyl, alkenyl, and alkoxy groups may be straight, cyclic, or branched chain groups. As used herein, unless otherwise indicated, the term "molecular weight" refers to weight average molecular weight, ($M_w$). The term "mass ratio" as used herein refers to ratio of the mass percentage of one component to the mass percentage of a second component, for example, two UV-absorbing polymers; two monomers that are used to react with one another in a polymerization reaction; or two repeat units that are present in a polymer after polymerization. Mass ratio can be expressed either as a ratio of percentages that add up to 100%, (e.g., 90%/10%) or in "ratio format" (e.g., 9:1).

UV-Absorbing Polymer

Embodiments of the invention relate to compositions including an ultraviolet radiation-absorbing polymer, (i.e., "UV-absorbing polymer"). By "UV-absorbing polymer," it is meant a polymer that absorbs radiation in some portion of the ultraviolet spectrum (290 nm-400 nm), and preferably has an extinction coefficient of at least about 1000 $mol^{-1}$ $cm^{-1}$, for example greater than 10,000 or 100,000 or 1,000,000 $mol^{-1}$ $cm^{-1}$, for at least one wavelength within the above-defined ultraviolet spectrum.

In one preferred embodiment, the UV-absorbing polymer has the chemical structure:

The UV-absorbing polymer generally includes n moles of a first repeat unit, A; and m moles of a second repeat unit, B. As such, the inventive UV-radiation absorbing polymer is a copolymer that has at least two repeat units. The polymer generally includes a backbone of covalently bonded carbon atoms (e.g., a carbon chain or C—C backbone) from which pendant groups are attached.

As will be recognized by those of skill in the art, the "backbone" refers generally to the portion of repeat units in a polymer that are covalently bonded to adjacent repeat units. If multiple such portions exist, the backbone is that portion of the polymer molecule having the largest number of continuous and covalently bonded atoms. Other smaller groups of covalently bonded atoms are considered pendant groups that branch from the backbone.

In one embodiment, the UV-absorbing polymer may be represented by the following chemical structure:

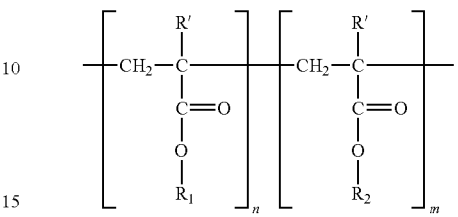

In this embodiment, the first repeat unit generally includes first pendant group, $R_1$ which is linked to the C—C backbone via, for example, a linking group, e.g., an ester linking group as shown above.

The C—C backbone generally consists of at least about 7 carbon atoms, preferably from about 7 to about 7000 carbon atoms, more preferably from about 10 to about 5000 carbon atoms, even more preferably from about 100 to about 4000 carbon atoms, and even more preferably from about 200 to about 3000 carbon atoms.

The first pendant group, $R_1$, includes a first UV-absorbing moiety (also referred to herein as a "UV-absorbing chromophore," a "UV chromophore," or, for simplicity a "chromophore"). The first UV-absorbing moiety absorbs in the ultraviolet spectrum.

In one particularly preferred embodiment, the first UV-absorbing moiety is a UV-A absorbing moiety. By "UV-A absorbing moiety," it is meant that the moiety has appreciable absorbance in the UV-A portion (320 nm to 400 nm) of the ultraviolet spectrum. For example, when a compound that includes the particular chemical moiety is cast into a film, it is possible to generate a molar extinction coefficient measured for at least one wavelength in this wavelength range of at least about 1000 $mol^{-1}$ $cm^{-1}$, preferably at least about 2000 $mol^{-1}$ $cm^{-1}$, more preferably at least about 4000 $mol^{-1}$ $cm^{-1}$. In a preferred embodiment, the molar extinction coefficient among at least 40% of the wavelengths in this portion of the spectrum is at least about 1000 $mol^{-1}$ $cm^{-1}$.

Examples of moieties that are UV-A absorbing include triazoles such as benzotriazoles; camphors such as benzylidene camphor and its derivatives (such as terephthalylidene dicamphor sulfonic acid also known as ECAMSULE or Mexoryl SX, available from L'Oreal); dibenzoylmethanes and their derivatives.

In a particularly preferred embodiment, the UV-absorbing moiety is a UV-absorbing triazole and/or a UV-absorbing benzoylmethane. In a further preferred embodiment, in order to provide both photostability and strong UV-A absorbance, the UV-absorbing moiety is a UV-absorbing triazole.

By "UV-absorbing triazole" it is meant UV-absorbing moiety containing a five-membered heterocyclic ring with two carbon and three nitrogen atoms. UV-absorbing triazoles include, for example, compounds of Formula I or II:

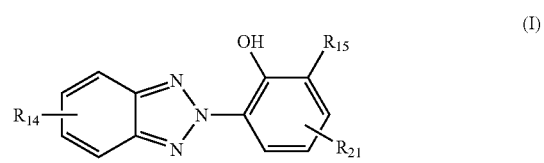

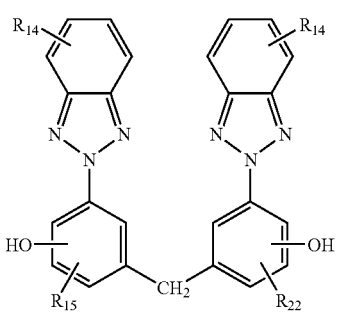

(II)

wherein each $R_{14}$ is independently selected from the group consisting of hydrogen, $C_1$-$C_{20}$ alkyl, alkoxy, acyl, alkyloxy, alkylamino, and halogen; each of $R_{15}$ and $R_{22}$ are independently selected from the group consisting of hydrogen, $C_1$-$C_{20}$ alkyl, alkoxy, acyl, alkyloxy, and alkylamino, at least one of $R_{15}$ and $R_{22}$ not being hydrogen; and $R_{21}$ is selected from $C_1$-$C_{20}$ alkyl, alkoxy, acyl, alkyloxy, and alkylamino.

In Formula I, either of the $R_{15}$ or $R_{21}$ groups may be oriented so as to be directly bonded to the (ester) linking group that connects the UV-absorbing triazole to the C—C backbone. In Formula II, either of the $R_{15}$ or $R_{22}$ groups may be oriented so as to be directly bonded to the (ester) linking group that connects the UV-absorbing triazole to the C—C backbone.

Monomeric compounds of Formulae I and II are described in U.S. Pat. No. 5,869,030, and include, but are not limited to, methylene bis-benzotriazolyl tetramethylbutylphenol (TINSORB M, Ciba Specialty Chemicals Corporation, Greensboro, N.C., USA). Other monomeric UV-absorbing dibenzoylmethanes include 2-(4-diethyl amino-2hydroxybenzol)-benzoic acid hexylkester, commercially available as UVINUL A Plus from BASF of Parsippany, N.J.

In one preferred embodiment, the UV-absorbing triazole is a compound of Formula I in which $R_{14}$ is a halogen, preferably chlorine, $R_{15}$ is a butyl group and $R_{21}$ is —$CH_2CH_2CO_2C_8H_{17}$ (which may be converted to an acid form and subsequently converted to an ethylenically unsaturated form in order to make it suitable for polymerization). Such UV-absorbing triazoles are available as a blend of octyl-3-[3-tert-butyl-4-hydroxy-5-(5-chhloro-2H-benzotriazol-2-yl)phenyl]propionate and its isomer, 2-Ethylhexyl-3-[3-tert-butyl-4-hydroxy-5-(5-chloro-2H-benzotriazol-2-yl)phenyl] propionate as TINUVIN 109, from Ciba Inc. (BASF Corporation). Another suitable example of a UV-absorbing triazole is a transesterification product of 2-[3'-tert-butyl-5'-(2-methoxycarbonylethyl)-2'-hydroxyphenyl]-2H-benzotriazole with polyethylene glycol 300, commercially available as TINUVIN 213, also available from Ciba Inc.

UV-absorbing dibenzoylmethanes include those that may be represented by Formula III:

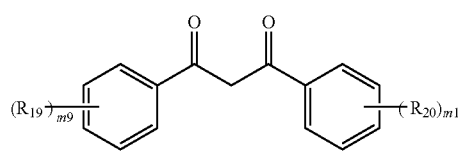

(III)

wherein $R_{19}$ and $R_{20}$, independently, are optionally $C_1$-$C_8$ alkyl or $C_1$-$C_8$ alkoxy, m9 is 0 to 3, and m10 is 1 to 3. Either of the $R_{19}$ and $R_{20}$ group may be oriented so as to be directly bonded to the (ester) linking group that connects the UV-absorbing dibenzoylmethane to the C—C backbone.

Examples and the synthesis of such monomeric dibenzoylmethane compounds compositions are disclosed in U.S. Pat. No. 4,489,057 and include, but are not limited to, 4-(1,1-dimethylethyl)-4'-methoxydibenzoylmethane (avobenzone and sold as PARSOL 1789, Roche Vitamins and Fine Chemicals, Nutley, N.J., USA), 2-2-methyldibenzoylmethane, 4-methyl-dibenzoylmethane, 4-isopropyldibenzoylmethane, 4-tert-butyldibenzoylmethane, 4-tert-butyl-4'-methoxydibenzoylmethane, 2,4-dimethylbenzoylmethane, 2,5-dimethylbenzoylmethane, 4,4'-diisopropylbenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, and 2,6-dimethyl-4-tert-butyl-4'-methoxydibenzoylmethane.

In another embodiment, the first ultraviolet-absorbing moiety is a UV-B absorbing moiety. By "UV-B absorbing moiety," it is meant that the moiety has appreciable absorbance in the UV-B portion (290 nm to 320 nm) of the ultraviolet spectrum. In one embodiment, the criteria for consideration as a UV-B absorbing moiety is similar to those described above for an UV-A absorbing moiety, except that the wavelength range is 290 nm to 320 nm.

Examples of suitable UV-B absorbing moieties include 4-aminobenzoic acid and alkane esters thereof; anthranilic acid and alkane esters thereof; salicylic acid and alkane esters thereof; hydroxycinnamic acid alkane esters thereof; dihydroxy-, dicarboxy-, and hydroxycarboxybenzophenones and alkane ester or acid halide derivatives thereof; dihydroxy-, dicarboxy-, and hydroxycarboxychalcones and alkane ester or acid halide derivatives thereof; dihydroxy-, dicarboxy-, and hydroxycarboxycoumarins and alkane ester or acid halide derivatives thereof; benzalmalonate (benzylidene malonate); benzimidazole derivatives (such as phenyl benzilimazole sulfonic acid, PBSA), benzoxazole derivatives, and other suitably functionalized species capable of copolymerization within the polymer chain.

Particularly suitable UV-B absorbing moieties include UV-absorbing benzophenones and UV-absorbing diphenylcyanoacrylate derivatives. Examples of benzophenone derivatives include those known in the art to provide protection of the skin from UV radiation, for example, such as taught by U.S. Pat. No. 5,776,439. Preferred compounds include 2-hydroxy-4-methoxybenzophenone ("oxybenzone") and 2-2'dihyroxy-4-methoxybenzophenone ("dioxybenzone") and diethylamine hydroxybenzoyl hexyl benzoate ("hydroxybenzophenone"). Examples of diphenylcyanoacrylate derivatives include 2-ethylhexyl 2-cyano-3,3-diphenyl-2-propenoate ("octocrylene") and its derivatives.

In one embodiment, the UV-absorbing polymer includes a single UV-absorbing moiety. In this embodiment, the single UV-absorbing moiety is preferably a UV-A absorbing moiety, and most preferably a UV-absorbing triazole.

In addition to the UV-absorbing moiety, the first repeat unit, A, of the UV-absorbing polymer, generally includes a functional group R', which may be, for example a hydrogen atom, alkyl group (e.g., $C_1$-$C_{12}$), or the like. In one embodiment, R has a molecular weight of less than about 100, such as less than about 50, such as less than about 30. In one preferred embodiment R' is a methyl group. It is preferred that the R' group is free of UV-absorbing moieties.

The molecular weight of the first repeat unit, A, may be from about 150 to about 1000, preferably from about 200 to about 700, more preferably from about 200 to about 500.

The number of first repeat units, n, per molecule (e.g., on average), may be from about 1 to about 6000, preferably from about 2 to about 3500, more preferably from about 5 to about 2500, and even more preferably from about 10 to about 1500.

The ultraviolet-radiation absorbing polymer generally includes m moles of a second repeat unit, B. The second repeat unit, B generally includes second pendant group, $R_2$ which is linked to the C—C backbone via, for example, an ester linking group.

The number of second repeat units, m, per molecule (e.g., on average), may be from about 2 to about 6300, preferably from about 3 to about 4000, more preferably from about 10 to about 3000, and even more preferably from about 20 to about 2000.

In one embodiment, the second pendant group is a "spacer group" that serves to provide an appropriate amount of space between UV-absorbing moieties ($R_1$) that are present throughout the UV-absorbing polymer. In this embodiment, the second pendant group is free of UV-absorbing moieties. As such, the second pendant group may also serve to facilitate intimate mixing with other components (e.g., hydrophobic components) in the composition.

Preferably, the spacer group is sufficient to maintain the hydrophobic character of the polymer. However, the spacer group should not confer such extraordinary hydrophobicity to the polymer such that it is difficult to dissolve, disperse, emulsify, or otherwise render the UV-absorbing polymer phase stable in a cosmetically acceptable carrier. As such, the second pendant group, $R_2$ of the second repeat unit, B, may include either or both of the following: (i) at least one siloxane (—Si—O—) linkage, such as from 1 to about 50 siloxane linkages, preferably from about 1 to about 20 siloxane linkages, and more preferably from about 1 to about 20 siloxane linkages, even more preferably from about 1 to about 16 siloxane linkages, even more preferably from 2 to 15 siloxane linkages, even more preferably from 2 to 10 siloxane linkages, and most preferably from 2 to 5 siloxane linkages.

In one preferred embodiment of the invention, the siloxane linkages are linearly arranged; in another embodiment the siloxane linkages are branched. The siloxane linkages may terminate in organic functional groups, e.g., an alkyl group, such as a methyl group; (ii) a hydrocarbon moiety, such as a hydrocarbon moiety having an intermediate number of carbon atoms. Suitable examples include $C_7$-$C_{16}$ hydrocarbon moieties, such as $C_7$-$C_{16}$ alkyl groups. In one preferred embodiment of the invention, such hydrocarbon moiety is linearly arranged; in another embodiment the hydrocarbon moiety is branched.

The second repeat unit, B, also includes a second functional group R', which may be the same or different than the first functional group R' of first repeat unit A. That is, second functional group R' may be, for example a hydrogen atom, alkyl group (e.g., $C_1$-$C_{12}$), or the like. In one embodiment, R' has a molecular weight of less than about 100, such as less than about 50, such as less than about 30. In one preferred embodiment R' is a methyl group. It is preferred that the R' group is free of UV-absorbing moieties.

The molecular weight of the second repeat unit, B, may be from about 100 to about 1000, preferably from about 100 to about 500, more preferably from about 100 to about 250.

The UV-absorbing polymers useful in the present invention are preferably "rich" in ultraviolet-absorbing moieties. As such they are highly suitable for formulation into topical sunscreens. By "rich" in ultraviolet-absorbing moieties, it is meant that the percentage by mole of first repeat units, n to total repeat units, n+m may be in a range from about 10% to about 100% (note that when the percentage is 100%, the spacer groups are entirely absent—in which case the UV-absorbing polymer may be a homopolymer with a C—C backbone and pendant groups with one or more UV-absorbing moieties, but no pendant groups that are free of UV-absorbing moieties). In certain preferred embodiments, the mole percentage of first repeat units, n, to total repeat units, n+m, is at least about 5% such as in a range from about 5% to about 90%, or 10% to about 90%, and in certain embodiments, such as from about 25% to about 70%. In certain embodiments, the mole percentage of first repeat units, n, to total repeat units, n+m is from about 25% to about 40%, such as from 30% to 40%.

In one embodiment, the ultraviolet absorbing polymer includes no repeat units other than repeat unit A and repeat unit B, described above. In another embodiment, the ultraviolet-radiation absorbing polymer includes one or more additional repeat units. These repeat units may include repeat units bearing an additional ultraviolet absorbing group, a siloxane group, a hydrocarbon group, or another organic moiety, or combinations of such groups such as may be linked to the C—C backbone via, for example, a ester linking group. The additional ultraviolet absorbing group may absorb over a similar spectral range as the first ultraviolet absorbing group present on repeat unit A. Examples of such UV-absorbing groups include benzotriazoles derivatives and benzophenone derivatives. In another embodiment, the additional ultraviolet absorbing group may absorb over a dissimilar spectral range as the first ultraviolet absorbing group.

Repeat unit A, repeat unit B and the additional repeat units may be arranged in various manners. For example, the repeat units may be arranged such they alternate, in blocks of various numbers of repeat units, or be randomly arranged.

The molecular weight of the ultraviolet radiation-absorbing polymer is sufficiently high enough to reduce the likelihood of absorption into the skin, and therefore the body. In one embodiment of the invention, the molecular weight of the ultraviolet radiation-absorbing polymer is greater than about 2000. In another embodiment, the molecular weight is high enough to reduce the likelihood of absorption into the skin, but not so high such that it is difficult to dissolve, disperse, emulsify, or otherwise make the UV-absorbing polymer phase stable in a cosmetically acceptable carrier. As such, the molecular weight of the UV-absorbing polymer may greater than about 2000, but not so high that the polymer becomes crosslinked. Preferably, the polymer is uncrosslinked. The molecular weight of the UV-absorbing polymer may be from about 2000 to about 1,000,000, preferably from about 50,000 and about 750,000, more preferably from about 50,000 to about 500,000. In one embodiment, the polymer is a linear polymer (i.e., includes no appreciable branching other than the presence of $R_1$, $R_2$, and R').

In order to reduce the likelihood of penetration of low molecular weight species through the skin, the ultraviolet radiation-absorbing polymer may have a (mass or number) fraction of low molecular weight species which is less than about 5%, such as less than about 1%, such as less than about 0.1%. By "low molecular weight species," it is meant those species that have a molecular weight that is less than about 2000.

In order to enhance water-resistance and spreadibility, the UV-absorbing polymer may, in certain embodiments have a low water solubility. For example, in certain embodiments, the ultraviolet radiation-absorbing polymer may have a water solubility that is less than about 3% by weight, preferably less than about 1% by weight. By "water solubility" it is meant the maximum weight percentage of polymer (relative to polymer plus water) that can be placed into 100 grams deionized water and agitated so that a clear solution is obtained and remains visually homogeneous and preferably transparent at room temperature for 24 hours.

Furthermore, in certain embodiments, the UV-absorbing polymer is desirably free of ionizable moieties that are commonly present in so-called "polymer latex" compositions to facilitate dispersion of the polymer in an aqueous system. Examples of ionizable moieties that, in this embodiment, may be absent include anionics such as sulfate, sulfonate, carboxylate, phosphate, phosphonates; cationics such as: ammonium, including mono-, di-, and trialkylammonium species, pyridinium, imidazolinium, amidinium, poly(ethyleneiminium; zwitterionics such as ammonioalkylsulfonate, ammonioalkylcarboxylate, amphoacetate. A UV-absorbing polymer free of ionizable moieties may form a more durable water repellant coating on the skin and enhance spreadability.

The ultraviolet radiation-absorbing polymer may have a melting point or a glass transition temperature that is, for example, below about 37° C.

It is further desirable that the UV-absorbing polymer have an absorbance in the UV that is sufficiently high so as to make it suitable for use as a sunscreen for the human body. In one embodiment, the polymer, when dissolved in a suitable solvent (e.g., DMSO, ethyl acetate, tetrahydrofuran, or the like) and spread or cast into a thin film, has a molar extinction coefficient measured for at least one wavelength within the UV spectrum, and more preferably in the UV-A spectrum, of at least about 1000 $mol^{-1}$ $cm^{-1}$, such as at least about 2000 $mol^{-1}$ $cm^{-1}$, such as at least about 4000 $mol^{-1}$ $cm^{-1}$, or even 10,000 or 100,000 or 1,000,000 $mol^{-1}$ $cm^{-1}$.

Polymers of the present invention may be synthesized, for example by methods known in the art. For example, suitable polymers may be formed by addition polymerization, such as via free-radical addition polymerization of suitable ethylenically unsaturated monomers. The resulting polymer may have its repeat units alternating, block, random, graft, star or other configurations.

For example, the inventive polymer may be made by reacting a first ethylenically unsaturated compound (monomer) that includes an ultraviolet-absorbing moiety, with a second compound (monomer) that includes, for example in one embodiment, at least one siloxane linkage. In another embodiment, the second ethylenically unsaturated monomer includes a hydrocarbon moiety, such as a hydrocarbon moiety having an intermediate number of carbon atoms. This reaction may take place in the presence of an initiator such as AIBN (azobisisobutyronitrile) or 1,1'-azobis(cyanocyclohexane) available as VAZO® VA-40 from E.I. DuPont of Wilmington, Del., or other suitable initiators. In one embodiment, the first ethylenically unsaturated compound includes a UV-A absorbing moiety. The UV-A absorbing moiety may be a benzotriazole. Examples of suitable benzotriazole monomers include 2'hydroxy-5'-methacryloxyethylphenyl-2H-benzotriazol as well as the methacrylated benzotriazole described in Examples 15 and 19 below. In another embodiment, the first ethylenically unsaturated compound includes a dibenzoylmethane. One such suitable monomer is a methacrylated dibenzoylmethane shown in Inventive Example 10 below.

The second ethylenically unsaturated compound may include a siloxane linkage, such as acryloxyalkyl polydimethylsiloxanes. One suitable example of such a monomer is monomethacryloxypropyl polydimethylsiloxane (mPDMS), such as mPDMS having average 11 siloxane linkages. Other monomers that include a siloxane that may be suitable include $C_{16}H_{38}O_5Si_4$, 2-Propenoic acid, 2-methyl-, 3-[3,3,3-trimethyl-1,1-bis [(trimethylsilyl)oxy]-1disiloxanyl]propyl ester (also known as "TRIS" monomer). mPDMS and TRIS are commercially available from Gelest Inc. of Morrisville, Pa.

In another embodiment, the second ethylenically unsaturated compound is an ethylenically unsaturated organosilane. By "ethylenically unsaturated organosilane" it is meant, any of various compounds that include at least one terminal Si-0-R linkage where R is a functional group such as an alkyl, aryl, aralkyl, among other functional groups. One particularly suitable ethylenically unsaturated organosilane is methacryloxypropyl trimethoxysilane (which has 3 siloxane linkages, from a common silicon atom), commercially available as Z-6030 from Dow Corning of Midland, Mich.

In another embodiment the second ethylenically unsaturated compound includes a hydrocarbon moiety, such as one having an intermediate number of carbon atoms. Suitable examples include acrylates or methacrylates having a $C_7$-$C_{16}$ alkyl attached thereto. Examples include a $C_8$ acrylate such as isooctyl acrylate $H_2C\!=\!CHCO_2(CH2)_5CH(CH_3)_2$; a $C_{12}$ methacrylate such as lauryl methacrylate, $H_2C\!=\!C(CH_3)CO_2(CH_2)_{11}CH_3$, and the like. Isooctyl acrylate and lauryl methacrylate are commercially available from Sigma-Aldrich of St. Louis, Mo.

Alternatively, the UV-absorbing polymer may be made by post-polymerization addition of the pendant groups to the polymer. For example, an acrylic polymer having a maleic anhydride functionality may be synthesized, followed by reaction of that polymer with a UV-monomer such as avobenzone, thereby chemically attaching the UV-absorbing moiety via an ester linkage. Suitable maleic anhydride copolymers include for example PA-18 (octadecene/maleic anhydride copolymer) commercially available from Chevron Phillips, or Gantrez AN copolymers (PVM/MA copolymer) commercially available from ISP. Alternatively, N-hydroxysuccinamide ester of (meth)acrylic acid can be used as a starting monomer.

Polymers of the present invention may be used, for Example by combining the polymer with a suitable cosmetically acceptable carrier as described below. The incorporation of polymers of the present invention into such compositions may provide enhanced SPF (primarily UV-B absorbance), enhanced PFA (primarily UV-A absorbance) or enhancement of both.

Topical Composition

In one embodiment, a composition, such as a composition suitable for topical/cosmetic use for application to the human body (e.g., keratinaceous surfaces such as the skin or hair), especially the skin, is provided. The composition includes the inventive UV-absorbing polymer described herein. The concentration of the inventive UV-absorbing polymer may vary from 0.001% to about 100% by weight, preferably from about 0.1% to about 50%, more preferably from about 0.5% to about 40% of the composition.

The compositions useful in the present invention may be used for a variety of cosmetic uses, including, especially for protection of the skin from UV radiation. The compositions, thus, may be made into a wide variety of delivery forms. These forms include, but are not limited to emulsions (W/O, O/W or multiple emulsions), dispersions, solutions, or coatings on water soluble or water-insoluble insoluble substrates (e.g., substrates such as organic or inorganic powders, fibers, or films). Suitable product forms including lotions, creams, gels, sticks, sprays, ointments, mousses, and compacts/powders. The composition may be employed for various end-uses, such as recreation or daily-use sunscreens, moisturizers, cosmetics/make-up, cleansers/toners, anti-aging products, or combinations thereof.

The compositions of the present invention may be prepared using methodology that is well known by an artisan of ordinary skill in the field of, for example, cosmetics formulation.

In certain preferred embodiments, compositions of the present invention include water and are thus "aqueous compositions." In certain further preferred embodiments, the composition is an emulsion that includes a water phase and an oil phase. It is particularly preferred that the composition includes a continuous water phase in which the UV-absorbing polymer is stabilized, preferably emulsified. The oil phase may be such that it is present in the emulsion in discrete droplets or units having an average diameter of about one micron to about 1000 microns, more preferably from about 1 micron to about 100 microns. In an alternative embodiment, the composition includes a continuous oil phase in which the water is stabilized, preferably emulsified.

The percentage of water included in the compositions may range from 10% to about 99%, preferably from about 20% to about 80%, more preferably from about 30% to about 70%.

Second UV-Absorbing Polymer

In one particularly preferred embodiment, the composition includes a second ultraviolet radiation-absorbing polymer. By "second ultraviolet radiation-absorbing polymer," it is meant a compound chemically distinct (with respect to chemical formula, e.g., chemical formula or repeat unit content) from the UV-absorbing polymer described above. Broadly speaking, the second UV-absorbing polymer may have one of various chemical backbones (e.g., siloxane or C—C) and one or more UV-absorbing moieties (UV-A and/or UV-B) either on one or more ends of the molecule or pending from the backbone. The second UV-absorbing polymer may have at least 2, more preferably at least about 10 repeat units.

In one embodiment, in order to enhance the synergy between the UV-absorbing polymer of the invention and the second UV-absorbing polymer, the molecular weight of the second UV-absorbing polymer is similar to the UV-absorbing polymer of the invention. As such, the second UV-absorbing polymer may have a molecular weight of at least 2000, such as at least about 5000, such as at least about 10,000. In one embodiment, the second UV-absorbing polymer has a molecular weight from about 5000 to about 200,000. Furthermore, the second UV-absorbing polymer may have solubility characteristics similar to those of the UV-absorbing polymer of the invention, as specified above (e.g., less than about 3% by weight water solubility, preferably less than about 1% by weight).

Applicants have found that UV-absorbance is surprisingly enhanced if a first UV-absorbing polymer is combined with a second UV-absorbing polymer, wherein the first UV-absorbing polymer and the second UV-absorbing polymer have particular features.

For example, in one aspect of the invention, compositions of the present invention include a first UV-absorbing polymer that includes a UV-A absorbing moiety and the second UV-absorbing polymer that includes a UV-B absorbing moiety. The UV-B absorbing moiety is different than the UV-A absorbing moiety. The first UV-absorbing polymer and the second UV-absorbing polymer are characterized as capable of providing both synergistic SPF and synergistic PFA protection over a mass percent range of the first and second UV-absorbing polymers of at least about 40% (defined below). In a preferred embodiment, the first UV-absorbing polymer and the second UV-absorbing polymer are characterized as capable of providing both synergistic SPF and synergistic PFA protection over a mass percent range of at least about 60%.

In order to assess whether a particular combination of two UV-absorbing polymers provides synergistic SPF protection, the following logarithmic SPF procedure may be used. SPF for (a) the first UV-absorbing polymer, (b) the second UV-absorbing polymer; and (c) the particular blend of the first UV-absorbing polymer and the second UV-absorbing polymer are determined. SPF is determined by forming a film with the polymer or composition to be tested and evaluating using the IN-VITRO SUN PROTECTION TEST METHOD that is described below.

In particular, if the SPF of each individual UV-absorbing polymer (Polymer A and Polymer B) is such that the logarithm of the SPF of the blend is higher than the sum of the logarithms of the unblended polymer components, each weighted by their respective mass fractions relative to the total mass of both UV-absorbing polymers, then the particular blend of UV-absorbing polymers provides synergistic SPF protection. The condition for synergy is thus specified below:

$$\text{Log SPF}_{blend} > X_A \text{ Log SPF}_A + X_B \text{ LOG SPF}_B$$

For example, if Log SPF of polymer A is 1 and Log SPF of polymer B is 1.2 and a blend of the 2 polymers (40% polymer A, 60% polymer B) has a Log SPF of greater than:

$$[(0.4) \times (1)] + [(0.6) \times (1.2)] = 1.12,$$

the particular blend provides synergistic SPF.

Similarly, synergistic PFA is determined in the same way. If $$\text{Log PFA}_{blend} > X_A \text{ Log PFA}_A + X_B \text{ LOG PFA}_B$$

the particular blend provides synergistic PFA protection.

PFA, like SPF, is determined according to the IN-VITRO SUN PROTECTION TEST METHOD, described below.

If the two UV-absorbing polymers can be blended into a single phase (either with a solvent system or with no ingredients other than the two polymers) and the blend provides both synergistic SPF and synergistic PFA protection, then the particular blend of Polymer A and Polymer B are "capable of providing both synergistic SPF and synergistic PFA protection."

By "solvent system," it is meant a solvent or a blend of solvents, oils, plasticizers or the like that are capable of simultaneously dissolving both UV-absorbing polymers over a range of concentrations.

Furthermore, if Polymer A and Polymer B are capable of providing both synergistic SPF and synergistic PFA protection for at least 3 different of mass ratios of the two polymers, (preferably at least 4 different mass ratios, more preferably at least about 5 different mass ratios—and each of the mass ratios that are measured are preferably spaced apart by at least 10%, such as 80%/20 and 70%/30), wherein the lowest concentration of the Polymer A and the highest concentration of the Polymer A are separated by at least about 40%, then the two polymers are capable of providing both synergistic SPF and synergistic PFA protection over a mass percent range of the two polymers of at least about 40%. Likewise, if the at least 3 different mass ratios are separated by at least about 60%, then the UV-absorbing polymers are capable of providing both synergistic SPF and synergistic PFA protection over a mass percent range of the two polymers of at least about 60%." For purposes of synergy assessment, by "about X %," it is meant within +/−1% of X %.

In certain preferred embodiments, (a) the first UV-absorbing polymer is a UV-absorbing polymer according to the invention, i.e., the first UV-absorbing polymer comprises a C—C backbone and includes a first pendant group that includes a UV-A absorbing moiety; and further includes a second pendant "spacer" group that includes either a siloxane linkage and/or intermediate number of carbon atoms; and furthermore (b) the second UV-absorbing polymer includes a UV-B absorbing moiety, different that the UV-A absorbing moiety.

In a preferred embodiment, the second UV-absorbing polymer also includes at least one siloxane (Si—O—) linkage, such as is preferably part of a siloxane backbone. In one embodiment, the siloxane backbone has at least about 10 siloxane linkages, such as at least about 50 siloxane linkages. In one preferred embodiment, the second UV-absorbing polymer is a dimethicodiethyl benzal malonate, also known as a benzylidene malonate silicone, such as the filter known as Polysilicone-15. Examples of suitable benzylidene malonate silicone include those described in U.S. Pat. No. 6,193,959 to Bernasconi et al. A particularly suitable benzylidene malonate silicone includes PARSOL SLX, commercially available from DSM (Royal DSM N.V.) of Heerlen, Netherlands.

Applicants have found that by utilizing blends that show synergy across a wide range of mass ratios, it is possible to provide compositions that have the benefit of non-penetrating sunscreens and enhanced protection across both UV-A and UV-B protection.

In another embodiment, the composition includes a first UV-absorbing polymer and the second UV-absorbing polymer that are capable of providing both synergistic SPF and synergistic PFA protection over a mass percent range of the two polymers of at least about 40%; and the composition further includes a synergy-promoting solvent system. "Synergy-promoting solvent system" means the following: the solvent system is such that when used to dissolve the UV-absorbing polymers, the UV-absorbing polymers provide a synergistic blend. In addition to the synergy promoting solvent system, the composition may have one or more other classes of ingredients suitable for personal care compositions.

The synergy promoting solvent system may be selected so as to dissolve both of the UV-absorbing polymers. As such, the components of the solvent system may have a solubility parameter that is similar to that of the UV-absorbing polymers. In one embodiment, the synergy promoting solvent system includes, consists essentially of, or consists of a solvent or plasticizer that does not absorb ultraviolet radiation and has a dielectric constant (i.e., static permittivity, measured at 20 degrees C.) that is from about 3 to about 8, more preferably from about 3 to about 6, and even more preferably from 4 to 6). Examples of suitable solvents are described in paragraph [0060] of published US patent application, US20090098367, entitled, "Compositions Having Elongated Particles With Varying Charges and Aspect Ratios," which is incorporated herein by reference.

In certain embodiments, the solvent is selected from a group consisting of: benzoate esters such as alkyl benzoate esters, in particular $C_{12}$-$C_{24}$ benzoate esters, such as a $C_{12}$-$C_{15}$ benzoate ester (e.g., FINSOLV TN, having a dielectric constant of about 3.8 commercially available from Finetex Inc. of Elmwood Park, N.J.); dibutyl adipate (e.g., CETIOL B, having a dielectric constant of about 5.1 commercially available from available from Cognis Corporation of Ambler, Pa.), caprylic/capric triglycerides (having a dielectric constant of about 3.8), and combinations thereof.

In another aspect, the composition of the present invention includes a first UV-absorbing polymer including a UV-A absorbing moiety; and a second UV-absorbing polymer including a UV-B absorbing moiety, wherein the first UV-absorbing polymer has a PFA/SPF ratio greater than 0.3 and the second UV-absorbing polymer has a PFA/SPF ratio less than 0.3. By selecting the first UV-absorbing polymer and the second UV-absorbing polymer to meet these requirements it is possible to achieve a composition having a PFA/SPF that is near or equal to 0.3, thus providing broad spectrum protection.

The first UV-absorbing polymer may be a UV-absorbing polymer of the invention. However, the first UV-absorbing polymer may have a siloxane backbone and/or have spacer groups different from those of the UV-absorbing polymer of the invention, and/or be devoid of spacer groups.

Furthermore in order to enhance the magnitude of both SPF and PFA and further provide a composition that has broad spectrum protection, Applicants have found that it is desirable for the composition to not only to include a first UV-absorbing polymer having a UV-A absorber, with a PFA/SPF ratio greater than 0.3; and a second UV-absorbing polymer having a UV-B absorber with a PFA/SPF ratio less than 0.3; but also for the two UV-absorbing polymers to provide both synergistic SPF and PFA protection at the particular mass ratio in which they are present in the composition. In this manner, the magnitude of SPF, and PFA are enhanced, but not at the expense of having a ratio that is removed from 0.3. In a related embodiment, the composition further includes a synergy-promoting solvent system.

In another aspect, the composition includes a first UV-absorbing polymer having a C—C backbone and including a UV-A absorbing moiety; and a second UV-absorbing polymer having a siloxane backbone and including a UV-B absorbing moiety.

The first UV-absorbing polymer may be formed by reacting two or more ethylenically unsaturated monomers. As such, it may have a first pendant group that includes the UV-A absorbing moiety. It may further include a second pendant group, such as a spacer group. In one embodiment, the first UV-absorbing polymer is a UV-absorbing polymer of the invention.

The second UV-absorbing polymer may have a variety of configurations. In one embodiment, the UV-absorbing moiety is present on the ends of the polymer. In a particularly desirable embodiment, the second UV-absorbing polymer includes a pendant group that includes the UV-B absorbing moiety.

Applicants have surprisingly found that the combination of a first UV-absorbing polymer having a C—C backbone and a UV-A absorber; and a second UV-absorbing polymer having a siloxane backbone and a UV-B absorber provides broad based synergy in SPF and PFA, whereas various other combinations of backbone type and UV-absorber type (e.g., UV-absorbing polymer having a C—C backbone and a UV-A absorber combined with a UV-absorbing polymer having a C—C backbone and a UV-B absorbing moiety) may not provide this desirable feature.

In another aspect, the composition includes a first UV-absorbing polymer having an C—C backbone, a first pendant group that includes a first UV absorber and a second pendant group comprising at least one siloxane group, wherein second pendant group is free of UV-chromophores; and a second UV-absorbing polymer that includes at least one siloxane (e.g., in its backbone, although this is not necessarily required) and a second UV absorbing moiety, different than the first UV-absorbing moiety.

Without wishing to be bound by theory, Applicants believe that the siloxane present in the second pendant group of the first UV-absorbing polymer enhances blending with the siloxane present in the second UV-absorbing polymer—thus providing enhanced ability to absorb UV-radiation.

In one preferred embodiment, the second UV-absorbing polymer includes at least one siloxane (Si—O—Si) linkage, such as may be a part of a siloxane backbone. In one embodiment, the siloxane backbone has at least about 10 siloxane linkages, such as at least about 50 siloxane linkages. In one preferred embodiment, the second UV-absorbing polymer includes a benzilydene malonate as a UV-absorbing group. One particularly suitable example is a dimethicodiethyl benzal malonate, also known as a benzylidene malonate silicone, such as the filter known as "Polysilicone-15." Examples of suitable benzylidene malonate silicone includes those described in U.S. Pat. No. 6,193,959 to Bemasconi et al. A particularly suitable benzylidene malonate includes "PARSOL SLX," commercially available from DSM (Royal DSM N.V.) of Heerlen, Netherlands.

In another embodiment, the second UV-absorbing polymer includes 2-cyano-3,3-diphenyl acrylic acid functional groups, such as are present in those polymeric sunscreens disclosed in U.S. Pat. Nos. 6,962,692; 6,899,866; and/or 6,800,274; including hexanedioic acid, polymerized with 2,2-dimethyl-1,3-propanediol, 3-[(2-cyano-1-oxo-3,3-diphenyl-2-propenyl)oxy]-2,2-dimethylpropyl 2-octyldodecyl ester. This polymer has a low molecular weight (less than 2000) and is sold under the trade name "POLYCRYLENE," commercially available from the HallStar Company of Chicago, Ill.

In another embodiment the composition further includes one or more inorganic ultraviolet screening compounds such as inorganic oxides including titanium dioxide, zinc oxide; iron oxides.

In one embodiment, the composition is free of monomeric sunscreens. In another embodiment, the composition may further comprise one or more additional UV-A and/or UV-B absorbers. Examples of such absorbing/reflecting agents include, but are not limited to "monomeric" organic UV filters: methoxycinnamate derivatives such as octyl methoxycinnamate and isoamyl methoxycinnamate; camphor derivatives such as 4-methyl benzylidene camphor, camphor benzalkonium methosulfate, and terephthalylidene dicamphor sulfonic acid; salicylate derivatives such as octyl salicylate, trolamine salicylate, and homosalate; sulfonic acid derivatives such as phenylbenzimidazole sulfonic acid; benzone derivatives such as dioxybenzone, sulisobenzone, and oxybenzone; benzoic acid derivatives such as aminobenzoic acid and octyldimethyl para-amino benzoic acid; octocrylene and other β,β-diphenylacrylates; dioctyl butamido triazone; octyl triazone; butyl methoxydibenzoyl methane; drometrizole trisiloxane; and menthyl anthranilate.

Other suitable UV absorbers/reflectors useful herein can be found in Sagarin, *Cosmetics Science and Technology*, Chapter VIII, pages 189 et seq. and the *ICI Handbook* page 1672. A list of such compounds is also disclosed in U.S. Pat. No. 4,919,934.

In certain embodiments the composition may include one or more compounds suitable for enhancing photostability. Photostabilizers include, for example, diester or polyesters of a naphthalene dicarboxylic acid. Examples of diesters and polyesters of a naphthalene dicarboxylic acid are compounds of formulae (X) or (XI):

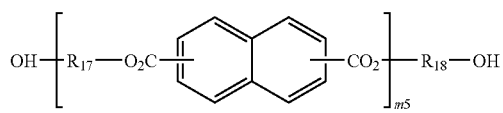

(X)

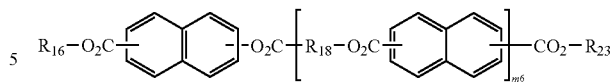

(XI)

wherein $R_{16}$ and $R_{23}$, independently, are selected from the group consisting of a $C_1$-$C_{22}$ alkyl, a diol having the structure HO—$R_{18}$—OH, and a polyglycol having the structure HO—$R_{17}$—(—O—$R_{18}$—)$_{m5}$—OH; $R_{17}$ and $R_{18}$, independently, are $C_1$-$C_6$ alkenyl; and m5 and m6, independently, are each in the range of 1 to about 100. Examples, including the synthesis, of such diesters or polyesters of naphthalene dicarboxylic acid are described in U.S. Pat. No. 5,993,789, and include, but not limited to, diethylhexyl naphthalate (HALLBRITE TQ, C.P. Hall Company, Bedford Park, Ill., USA). See Bonda, et al., *Allured's Cosmetic & Toiletries Magazine*, 115(6):37-45 (2000) disclosing the uses of such compounds in sunscreen compositions. In one embodiment, the diester or polyester of a naphthalene dicarboxylic acid can range from about 0.1% to about 30%, by weight, of the total composition (e.g., from about 1% to about 10%, by weight). Other photostabilizers that may be suitable include butyloctyl salicylate, bemotrizanol, diethylhexyl syringylidenemalonate, tris(tetramethylhydroxypiperidinol) citrate, polyester-8, octocrylene, ethylbenzilidene camphor, oxybenzone, amide oils, arylakylbenzoates among other photostabilizers.

In one embodiment, the composition further comprises an alkyl benzoate derivative. Examples of alkyl benzoate derivatives are compounds of the formulae (XII) or (XIII):

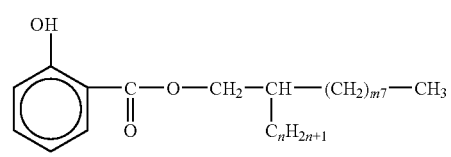

(XII)

wherein m7 is 5, 7, or 9 and n is 4, 6, or 8;

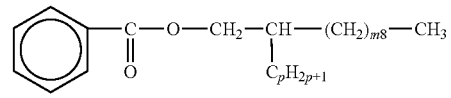

(XIII)

wherein m8 is 5 or 7 and p is 4 or 6.

The compounds of formulae (XII) and (XIII) may be formed by typical esterification and transesterification reactions, e.g., as describe in U.S. Pat. No. 5,783,173. Examples of such long branched chain alkyl benzoates are listed in U.S. Pat. No. 5,783,173 and include, but not limited to, butyloctyl salicylate (HALLBRITE BHB, C.P. Hall Company, Bedford Park, Ill., USA). In one embodiment, the alkyl benzoate derivative can range from about 0.1% to about 30%, by weight, of the total composition (e.g., from about 1% to about 10%, by weight).

The compositions of the present invention may further comprise one or more other cosmetically active agent(s). A "cosmetically active agent" is a compound that has a cosmetic or therapeutic effect on the skin, e.g., agents to treat wrinkles, acne, or to lighten the skin. In one embodiment, the agent is selected from, but not limited to, the group consisting of:

hydroxy acids; benzoyl peroxide; sulfur resorcinol; D-panthenol; hydroquinone; anti-inflammatory agents; skin lightening agents; antimicrobial and antifungal agents such a miconazole, ketoconazole, and elubial; vitamins such as ascorbic acid; tocopherols and tocotrienols such as tocopheryl acetate; retinoids such retinol, retinal, retinyl palmitate, retinyl acetate, and retinoic acid; hormones such as estrogens and dihydroxyandrostene dione; 2-dimethylaminoethanol; lipoic acid; amino acids such a proline and tyrosine; lactobionic acid; self-tanning agents such as dihydroxy acetone; dimethyl aminoethanol; acetyl-coenzyme A; niacin; riboflavin; thiamin; ribose; electron transporters such as NADH and FADH2; botanical extracts such as ginkgo biloba, aloe vera, and soy; and derivatives thereof. The cosmetically active agent will typically be present in the composition of the invention in an amount of from about 0.001% to about 20% by weight of the composition, e.g., about 0.01% to about 10% such as about 0.1% to about 5% by weight of the composition.

Examples of hydroxy acids include, but are not limited, to (i) alpha-hydroxy acids such as glycolic acid, lactic acid, malic acid, citric acid, and tartaric acid, (ii) beta-hydroxy acids such as salicylic acid, and/or (iii) polyhydroxy acids. See, e.g., European Patent Application No. 273,202.

Examples of derivatives of ascorbic acid include, but are not limited to, ascorbyl palmitate, magnesium ascorbyl phosphate, sodium ascorbyl phosphate, zinc ascorbyl phosphate, ascorbyl glucoside, sodium ascorbate, and ascorbyl polypeptide. An example of a derivative of hydroquinone includes, but is not limited to, arbutin.

The compositions of the present invention may also comprise one or more of the following: antioxidants (e.g., ascorbic acid, tocopherols, polyphenols, tocotrienols, BHA, and BHT), chelating agents (e.g., EDTA), and preservatives (e.g., parabens). Examples of suitable antioxidants, preservatives, and chelating agents are listed in pp. 1612-13, 1626, and 1654-55 of the *ICI Handbook*. In addition, the topical compositions useful herein can contain conventional cosmetic adjuvants, such as dyes, opacifiers (e.g., titanium dioxide), pigments, and fragrances.

The one or more UV-absorbing compounds in the composition may be combined with a "cosmetically-acceptable topical carrier," i.e., a carrier for topical use that is capable of having the other ingredients dispersed or dissolved therein, and possessing acceptable properties rendering it safe to use topically. As such, the composition may further include any of various functional ingredients known in the field of cosmetic chemistry, for example emulsifiers, emollients/oils/waxes, humectants, thickeners, opacifiers, fragrances, dyes, co-solvents among other functional ingredients. Furthermore, the composition may be essentially free of ingredients that would render the composition unsuitable for topical use. As such, the composition may be essentially free of solvents such as volatile solvents, and, in particular, free of volatile organic solvents such as ketones, xylene, toluene, and the like. By "essentially free" it is meant that such ingredients are present individually or in combination in concentrations of less than about 2%, preferably less than about 1%, more preferably less than about 0.5%, and most preferably free of such compounds.

In certain embodiments the composition has a pH that is from about 4.0 to about 8.0, preferably from about 5.5 to about 7.0.

In one particularly notable embodiment, the composition includes an emulsifier suitable for stabilizing the UV-absorbing polymer, such as in an oil in water emulsion. Suitable emulsifiers, e.g., such as non-ionic emulsifiers, include those commonly used in personal care products such as alkyl/fatty alcohols, alkyl/fatty esters, alkyl/fatty glucosides, alkoxylated esters fatty acids, and the like. In another embodiment, the composition includes one or more oils or other hydrophobic compounds to aid in spreading and or solubilization of the UV-absorbing polymer. Suitable hydrophobic compounds include oils including mineral oils, petrolatum, vegetable or animal-derived oils (triglycerides and the like); non-hydrocarbon based oils such as dimethicone, and other silicone oils as well as silicone gums; fragrance oils; waxes including polyethylene waxes, and other mixtures of fatty esters, not necessarily esters of glycerol.

The compositions of the present invention can be used by topically administering to a mammal, e.g., by the direct laying on or spreading of the composition on the skin or hair of a human.

The compositions of the present invention may be prepared using methodology that is well known by an artisan of ordinary skill. Specific examples of inventive polymers, methods, and compositions are described below.

Compositions according to various embodiments of the present invention confer one or more important advantages when compared with prior art compositions. According to certain embodiments, the compositions include UV-absorbing polymers having a C—C backbone and these often confer various advantages over those with siloxane backbones. These advantages include, but are not limited to: greater flexibility in preparation (emulsion, solution, bulk, solution), and/or initiation routes, and/or the ability to produce higher molecular weights and tailor molecular weight and its distribution and/or reduced contamination by unreacted monomer.

Other potential advantages include the ability to tailor the placement and sequence of the pendant UV-absorbing chromophore and pendant siloxane groups, thereby enhancing the likelihood of achieving the desirable combination of (a) achieving sufficiently high UV-chromophore levels in the polymer, thereby reducing the concentration of polymer needed in the ultimate topical sunscreen composition, and thus creating a variety of sunscreen formulation schemes.

Applicants have also surprisingly found that UV-absorbing polymers according to certain embodiments of the invention can be made with the appropriate molecular weight necessary to reduce skin penetration. They can also be made sufficiently hydrophobic so as to avoid insufficient water-repellency (as may be common in polymer lattices or polymers with too much hydrophilic character), yet still be sufficiently easy to formulate, have sufficient spreadibility on the skin, and yet can still be economically produced.

Furthermore, according to certain embodiments of the invention, C—C backbone, UV-absorbing polymers possess the ability to be blended with other UV-absorbing materials to create a desirable balance of UVA/UVB protection. Such blends may also be formulated with superior aesthetics without necessarily requiring that the formulation include additional silicone in the form of silicone oils. Such formulations achieve a high degree of spreading, as well as waterproofing due to the UV-absorbing polymer's low water solubility.

The following Examples further illustrate the invention.

Examples 1-3

Preparation of UV-Absorbing Polymers

The following UV-absorbing polymers according to the invention were synthesized according to the following process: an ethylenically unsaturated monomer containing a UV-absorbing group, 2-(2'hydroxy-5'-methacryloxyethylphenyl)-2H-benzotriazol, having a molecular weight of 292 grams/mol (referred to herein as "NORBLOC") was dissolved in ethyl acetate solvent and added to a three-neck, 100 ml round bottom flask. Twenty five grams of a second ethylenically unsaturated monomer, monomethacryloxypropyl polydimethylsiloxane (mPDMS—includes 10 siloxane repeat units per molecule; molecular weight about 900 grams/mol) was then added.

Under reflux, the reaction mixture was stirred at 65° C. (±15° C.) until fully dissolved and was purged with nitrogen for 30 minutes. Azobisisobutyronitrine (AIBN; molecular weight 146.21 g/mol) was then added using a syringe. The reaction stirred for 16-18 hours and was monitored by TLC for the loss of NORBLOC. Once the reaction was complete, 100-200 ml of toluene was added to the mixture and heated to 80° C. while stirring. The reaction was cooled to ambient temperature and 500 ml of ice-cold methanol was added precipitating out the polymer. Two additional washes of the precipitate with 500 ml of ice-cold methanol were performed removing any unreacted monomers. The precipitate was dissolved in ethyl acetate, concentrated down by rotary evaporation and put under vacuum for 24 hours.

Three polymers, Examples 1-3, were separately prepared by varying the amount of NORBLOC and AIBN. The amount of solvent used was 4, 7, and 10 g, respectively. The percentages by weight of reactants (i.e., NORBLOC and mPDMS), are as shown in Table 1 below:

TABLE 1

|  | Example | | |
| --- | --- | --- | --- |
|  | Ex. 1 | Ex. 2 | Ex. 3 |
| mPDMS | 95.15% | 91.35% | 86.72% |
| Norbloc | 4.17% | 8.00% | 12.66% |
| AIBN | 0.68% | 0.65% | 0.62% |

Table 2 shows the molar ratios, as calculated, for the reactants for the same examples:

TABLE 2

|  | Example | | |
| --- | --- | --- | --- |
|  | Ex. 1 | Ex. 2 | Ex. 3 |
| mPDMS | 83.33% | 74.08% | 64.56% |
| Norbloc | 12.50% | 22.22% | 32.28% |
| AIBN | 4.17% | 3.70% | 3.16% |

The polymers were analyzed by Gel Permeation Chromatography for various measures of molecular weight, and polydispersity. The results are shown in Table 3 below:

TABLE 3

|  | Example | | |
| --- | --- | --- | --- |
|  | Ex. 1 | Ex. 2 | Ex. 3 |
| Mw | 684,057 | 166,459 | 162,957 |
| Mn | 88,194 | 51,173 | 59,505 |
| Mz | 3,480,297 | 478,776 | 425,511 |
| Mw/Mn | 7.76 | 3.26 | 2.74 |
| MP | 166,723 | 99,588 | 98,728 |
| Mz + 1 | 7,009,308 | 1,059,361 | 856,469 |
| Polydispersity | 7.68 | 3.28 | 2.65 |

Examples 4-8

Preparation of UV-Absorbing Polymers and NORBLOC Homopolymer

UV-absorbing polymers according to the invention similar to those of Examples 1-3 were prepared, except that the mass of solvent was varied (5 grams for Ex. 4 and 30 ml for Ex. 5-8). The amounts of AIBN and NORBLOC were also varied. Ex. 8 was prepared as a homopolymer (no mPMDS). The mole percents of reactants are given in Table 5 below:

TABLE 5

|  | Example | | | | |
| --- | --- | --- | --- | --- | --- |
|  | Ex. 4 | Ex. 5 | Ex. 6 | Ex. 7 | Ex. 8 (comparative) |
| mPDMS | 80.0% | 48.9% | 29.8% | 6.7% | 0.00% |
| Norbloc | 16.0% | 48.4% | 68.1% | 91.9% | 96.4% |
| AIBN | 4.0% | 2.7% | 2.1% | 1.4% | 3.6% |

Example 9

UV-Absorbance at 5 Wt. Percent Chromophore—Comparison of UV-Absorbing Polymers and NORBLOC Homopolymer The UV-absorbing polymers of Ex. 6, Ex. 5, and the homopolymer of Ex. 8 were each separately dissolved in THF. The concentration of polymer was chosen such that in each case the total concentration of chromophore in solution was 5%. Each solution was tested according to the "IN-VITRO SUN PROTECTION TEST METHOD" described below.

In-Vitro Sun Protection Test Method:

The baseline transmission of a PMMA plate (substrate) without application of any test materials applied thereto was measured. Test samples were prepared by providing a sample of polymer. (Blends may also be tested by this method. The polymer(s) can be tested without any additional additives; with a solvent system, or as a part of a personal care composition that may include solvent and/or additional ingredients.)

Each sample was separately applied to a PMMA plate (available from Helioscience, Marseille, France) using an application density of 2 micro liters of solution per square centimeter of substrate, rubbing in into a uniform thin layer with the operator's finger, and allowed to dry. Three such samples were done for each test material. The samples were then allowed to dry for 15 minutes before measurement of absorbance using calibrated Labsphere® UV-1000S UV transmission analyzer (Labsphere, North Sutton, N.H., USA). The absorbance measures were used to calculate SPF and PFA indices (biological protection factor in the UVA based).

SPF and PFA were calculated using methods known in the art—see equation (1) below for calculation of SPF:

$$SPF_{in\ vitro} = \frac{\int_{\lambda=290nm}^{\lambda=400nm} E(\lambda) * I(\lambda) * d\lambda}{\int_{\lambda=290nm}^{\lambda=400nm} E(\lambda) * I(\lambda) * 10^{-A_0(\lambda)} * d\lambda} \quad (1)$$

where:

E(λ)=Erythema action spectrum

I(λ)=Spectral irradiance received from the UV source

A0(λ)=Mean monochromatic absorbance of the test product layer before UV exposure dλ=Wavelength step (1 nm)

The calculation of PFA (i.e., UVAPF) is calculated in a similar manner, except that the wavelength range is 320 nm to 400 nm.

FIG. 1 shows the absorbance spectra for the UV-absorbing polymers of Examples 5 and 6 and the homopolymer of Example 8.

PFA and SPF were calculated and are shown in Table 6, below:

TABLE 6

| Polymer | % Polymer in Solution | % Chromophore in Solution | SPF | PFA |
|---|---|---|---|---|
| Ex. 8 | 5 | 5 | 7.2 | 5.9 |
| Ex. 6 | 12.5 | 5 | 15.3 | 9 |
| Ex. 5 | 20 | 5 | 15 | 7.6 |

The results indicate that the copolymers of Ex. 5 and Ex. 6, each of which includes the "spacer" repeat unit, mPDMS, quite surprisingly had higher SPF and PFA than the homopolymer of Ex. 8, even though each sample contained the same amount of total chromophore. Thus, it appears that by using mPDMS as a comonomer, a surprisingly beneficial improvement in UV-absorbance is achieved as compared with a polymer in which such a spacer is absent.

Example 10

The following prophetic example is provided for synthesizing a UV-absorbing polymer of the invention. The polymer is similar to the polymer of Examples 4-7, except that the UV-absorbing group is a dibenzoylmethane.

Step 1—Protection of the phenol: In this step, avobenzone is reacted with a dihydropyran to protect the phenolic hydroxyl group.

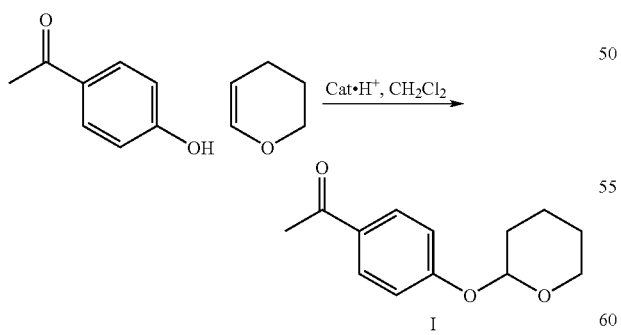

Step 2—Coupling reaction to prepare the beta diketone (condensation): In this step, the beta diketone is prepared by making a solution of the enolate, and adding the acid chloride dropwise. Excess of the enolate relative to the beta diketone is used.

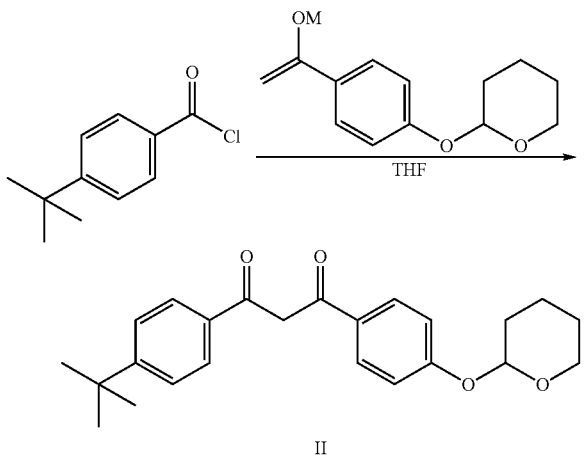

Step 3—Deprotection of the THP ether

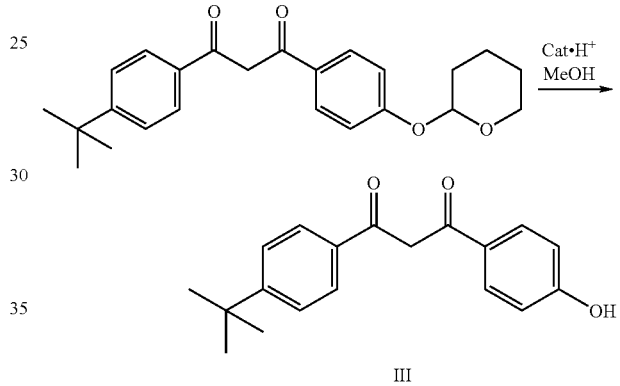

Step 4—Methacrylation of the phenol: In this step methacrylated dibenzoylmethane (an ethylenically unsaturated monomer) is prepared by esterifaction with methacrylic anhydride.

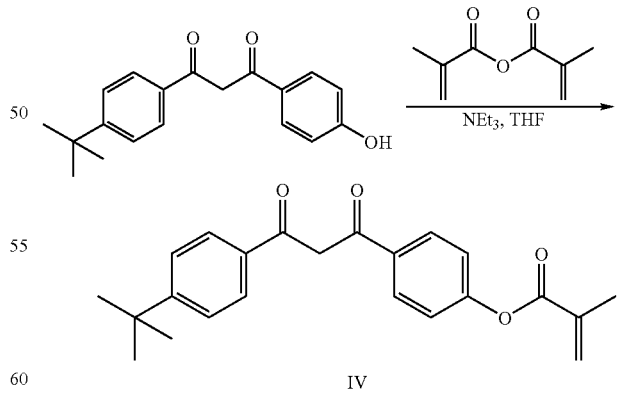

Step 5—Polymerization: An acrylic copolymer of dibenzoylmethane and mPDMS is prepared in a manner similar (AIBN initiated polymerization, precipitation addition via cold methanol) to the method for synthesizing the polymers described above, with reference to Examples 1-4.

Example 11

The UV-absorbing polymer of Ex. 3 was blended with a second UV-absorbing polymer, PARSOL SLX. The polymer of Ex. 3, PARSOL SLX, and various blends of the two were tested for SPF and PFA. No additional ingredients (e.g., solvents, oils, etc.) were added to the test samples. Table 7 below shows the results.

TABLE 7

| Polymer Blend | SPF | PFA | PFA/SPF |
|---|---|---|---|
| Ex. 3, Pure | 14.8 | 6.5 | 0.44 |
| Parsol SLX, Pure | 16.7 | 1.1 | 0.07 |
| 50% Ex. 3, 50% SLX | 64.7 | 6.4 | 0.10 |
| 60% Ex. 3, 40% SLX | 34.5 | 4.8 | 0.14 |
| 80% Ex. 3, 20% SLX | 47.0 | 7.8 | 0.17 |
| 95% Ex. 3, 5% SLX | 27.8 | 7.5 | 0.27 |
| 96% Ex. 3, 4% SLX | 23.9 | 7.0 | 0.29 |
| 98% Ex. 3, 2% SLX | 28.4 | 8.4 | 0.30 |

The results indicate that when controlled for total amount of sunscreen, the blends of Ex. 3 and PARSOL SLX showed significantly better performance than either polymer alone. This indicates, surprisingly, that synergistic UV-absorbance is provided by the various blends of a UV-absorbing polymer according to the invention, having a C—C backbone, a pendant UV-A group and a pendant spacer group that includes a siloxane, which polymer is free of ionizable moieties, with a siloxane-backbone polymer having UV-B absorbing moieties. The results show that it is further possible to provide the particularly desirable but typically difficult to achieve combination of high values of SPF (e.g., greater than 20), high PFA (e.g., greater than 5), and high ratio of PFA/SPF (e.g., greater than 0.2).

Example 12

The following personal care composition, shown below in Table 8, was made using emulsification techniques known in the art of cosmetic chemistry. The composition was a water in oil emulsion (water as the exterior phase) and included two UV-absorbing polymers, emulsifiers (SIMUSOL, MONTANOV) that served to emulsify the UV-absorbing polymer, a humectant (glycerin), preservatives, a thickener (SIMULGEL polymer), and pH adjusters.

A main vessel was charged with water, to which glycerine, parabens, and phenoxyethanol were added. The vessel was then heated gradually to 75° C. An oil phase premix was made by mixing the polymer of Ex. 6 with PARSOL SLX and DC 246, SIMUSOL, MONTANOV, and cocoate BG. The oil phase premix was then heated slowly to 75° C. Once the two vessels reached 75° C., the oil phase premix was added to the main vessel. They were mixed for 15 minutes and held at 75° C. After 15 minutes, SIMULGEL was added and mixed for 5 minutes while the vessel was kept at 75° C. The vessel was then slowly cooled to 30° C. and pH was adjusted to between 5 and 6 with citric acid or sodium hydroxide.

TABLE 8

| Trade name | INCI or CTFA name | Wt. % |
|---|---|---|
| water | aqua | 68 |
| glycerine | Glycerin | 3 |
| methyl paraben | Metylparaben | 0.2 |
| propyl paraben | Propylparaben | 0.1 |
| phenoxyethanol | Phenoxyethanol | 0.7 |
| Polymer of Inventive example, Ex. 6 | Polymer | 10 |
| PARSOL SLX | Polysilicone-15 | 1 |
| DC246 | Cyclohexasiloxane and Cyclopentasiloxane | 3 |
| SIMUSOL 165 | PEG-100 Stearate and Glyceryl Stearate | 1 |
| MONTANOV 68 | Cetearyl Alcohol and Cetearyl Glucoside | 3 |
| cocoate BG | Butylene Glycol Cocoate | 10 |
| SIMULGEL EG | Sodium Acrylate/Sodium Acryloyldimethyl Taurate Copolymer and Isohexadecane and Polysorbate 80 | 0.5 |
| citric acid | citric acid | 0.1 |
| sodium hydroxide | sodium hydroxide | 0.1 |

The composition had good spreadability and did not leave any brittle, flaky residue on the skin.

Example 13A

Preparation of UV-Absorbing Polymer

The following UV-absorbing polymer of the invention was synthesized according to the following process. 4.6 grams of a first ethylenically unsaturated monomer, isooctyl acrylate ($H_2C\!=\!CHCO_2(CH_2)_5CH(CH_3)_2$); molecular weight 184.3 grams/mol) and 8 grams of NORBLOC, were added to a three-neck, 500 ml round bottom flask equipped with an addition funnel. 50 ml of ethyl acetate was then added. 7.4 grams of isooctyl acrylate and 10 ml of ethyl acetate were added to the addition funnel, attached to the flask.

Under reflux, the reaction mixture was stirred at 65° C. (±15° C.) until fully dissolved and was purged with nitrogen for 30 minutes. 200 mg. Of azobisisobutyronitrine (AIBN; 146.21 g/mol) was dissolved in 5 ml of ethyl acetate and then added using a syringe. The isooctyl acrylate/ethyl acetate solution was then added dropwise over a period of 90 minutes into the reaction solution. The reaction stirred for 16-18 hours and was monitored by TLC for the loss of NORBLOC. Once the reaction was complete, the reaction was cooled to 25 C. 500 ml of ice cold methanol was added, precipitating out the copolymer. Two additional washes were performed removing any unreacted monomers. The precipitate was put under vacuum for 24 hours. Product yield was 75% (15 g) by weight percent. The mass ratio of NORBLOC to isooctyl acrylate was 40%/60%=2:3.

Example 13B

Preparation of UV-Absorbing Polymer

A synthesis similar to Example 13A was conducted, however, the amounts of reactants and solvents were scaled up to approximately 10 times the amounts listed in Example 13A. Before the ice-cold methanol was added, 200-400 ml of the ethyl acetate solvent was removed using a rotary evaporator. One liter of ice cold methanol was added to precipitate the copolymer. The subsequent washing was conducted as above. Yield was 75% (150 grams of polymer). The mass ratio of NORBLOC to isooctyl acrylate was 40%/60%=2:3.

Example 14

Blends of four separate combinations of UV-absorbing polymers in a solvent system were prepared. In each case, the blends consisted of 90% by weight of solvent and 10% by weight of a mixture of two UV-absorbing polymers. The blends were prepared by dissolving two UV-absorbing polymers in a solvent system consisting of FINSOLV TN and FINSOLV TPP. The solvent system was 98.89% FINSOLV TN and 1.11% FINSOLV TPP. After dissolving the UV-absorbing polymer, the resulting solution was 89% FINSOLV TN, 1% FINSOLV TPP (itself a blend of 3 benzoate esters), and 10% total UV-absorbing polymer(s). Similarly, solutions of single polymers in the solvent system were also prepared. The selection and mass ratio of UV-polymers was varied as shown in Table 9 below:

solution a dark, amber orange color. The reaction stirred for 24 hours and was monitored by TLC. After the reaction was complete about 900 mL of solvent was distilled off by rotary evaporation. 1N HCl (aq) was added, until a pH of 1 was achieved by litmus paper, precipitating a white precipitate. The white precipitate was filtered and washed with 1N HCl (aq) 3×1 L. It was then redissolved in 1 L CHCl$_3$ and an organic extraction was performed with 2×600 mL 1N HCl (aq). The organic layer was collected, dried over anhydrous Na$_2$SO$_4$, filtered, concentrated down by rotary evaporation and dried under vacuum overnight at 50° C., to form an acid form of TINUVIN 213, with a yield of about 90%.

TABLE 9

| Ref. # | Polymer Blend | SPF | log SPF | log SPF* | SPF synergy (Y/N) | PFA | log PFA | log PFA* | PFA synergy (Y/N) | PFA/SPF |
|---|---|---|---|---|---|---|---|---|---|---|
| Ex. 14a | Polymer of Ex. 6 | 4.820 | 0.683 | — | — | 3.320 | 0.521 | — | — | 0.689 |
| Ex. 14b | Parsol SLX | 3.700 | 0.568 | — | — | 0.800 | −0.097 | — | — | 0.216 |
| Ex. 14c | Ex. 6 90%/10% SLX | 4.800 | 0.681 | 0.672 | Y | 3.000 | 0.477 | 0.459 | Y | 0.625 |
| Ex. 14d | Ex. 6 50%/50% SLX | 6.300 | 0.799 | 0.626 | Y | 2.200 | 0.342 | 0.212 | Y | 0.349 |
| Ex. 14e | Ex. 6 60%/40% SLX | 5.900 | 0.771 | 0.637 | Y | 2.400 | 0.380 | 0.274 | Y | 0.407 |
| Ex. 14f | Ex. 6 10%/90% SLX | 4.300 | 0.633 | 0.580 | Y | 1.000 | 0.000 | −0.035 | Y | 0.233 |
| Ex. 14a | Polymer of Ex. 6" | 4.820 | 0.683 | — | — | 3.320 | 0.521 | — | — | 0.689 |
| Ex. 14g | Polycrylene ("PC") | 3.000 | 0.477 | — | — | 1.000 | 0.000 | — | — | 0.333 |
| Ex. 14h | Ex. 6 90%/10% PC | 6.900 | 0.839 | 0.662 | Y | 4.000 | 0.602 | 0.469 | Y | 0.580 |
| Ex. 14i | Ex. 6 50%/50% PC | 3.000 | 0.477 | 0.580 | N | 1.900 | 0.279 | 0.261 | Y | 0.633 |
| Ex. 14j | Ex. 6 60%/40% PC | 3.700 | 0.568 | 0.601 | N | 2.400 | 0.380 | 0.313 | Y | 0.649 |
| Ex. 14k | Ex. 6 10%/90% PC | 2.900 | 0.462 | 0.498 | N | 1.100 | 0.041 | 0.052 | N | 0.379 |
| Ex. 14l | Polymer of Ex. 13A | 5.900 | 0.771 | — | — | 3.600 | 0.556 | — | — | 0.610 |
| Ex. 14g | Polycrylene ("PC") | 3.000 | 0.477 | — | — | 1.000 | 0.000 | — | — | 0.333 |
| Ex. 14m | Ex. 13A 90%/10% PC | 5.500 | 0.740 | 0.741 | N | 3.300 | 0.519 | 0.501 | Y | 0.600 |
| Ex. 14n | Ex. 13A 60%/40% PC | 4.500 | 0.653 | 0.653 | N | 2.500 | 0.398 | 0.334 | Y | 0.556 |
| Ex. 14l | Polymer of Ex. 13A | 5.900 | 0.771 | — | — | 3.600 | 0.556 | — | — | 0.610 |
| Ex. 14b | Parsol SLX | 3.700 | 0.568 | — | — | 0.800 | −0.097 | — | — | 0.216 |
| Ex. 14o | Ex. 13A 90%/10% SLX | 6.740 | 0.829 | 0.751 | Y | 3.480 | 0.542 | 0.491 | Y | 0.516 |
| Ex. 14p | Ex. 13A 60%/40% SLX | 6.100 | 0.785 | 0.690 | Y | 2.600 | 0.415 | 0.295 | Y | 0.426 |
| Ex. 14q | Ex. 13A 10%/90% SLX | 6.050 | 0.782 | 0.588 | Y | 1.300 | 0.114 | −0.032 | Y | 0.215 |

In order to test for synergy, log SPF* and log PFA* were calculated using the mass percent of each of the UV-absorbent polymers in the blend. As discussed previously, if log SPF>log SPF*, synergy was recorded in the above table as "Y" for yes or "N" for no. Similar calculations were performed for log PFA*.

The blend of Ex. 6 and PARSOL SLX provided synergy in both SPF and PFA across the entire mass percent range tested—a concentration range of 80%.

The blend of Ex. 13A and PARSOL SLX provided synergy in both SPF and PFA across the entire concentration range tested—a concentration range of 80%.

The blend of Ex. 6 and POLYCRYLENE provided synergy PFA only across a concentration range (90-60) of 30%, whereas synergy was only identified at one particular concentration (Ex. 14h; 90% Ex. 6, 10% PC) for SPF.

The blend of Ex. 13A and POLYCRYLENE provided synergy PFA synergy for the two concentrations tested, whereas no synergy was provided in SPF.

Example 15

Preparation of UV-Absorbing Monomer

An acid form of TINUVIN 213 (Ciba, Inc) was prepared, as follows: 40.0 g of TINUVIN 213 was added to a 2 liter, round bottom flask equipped with a stir bar and addition funnel. 1 liter of methanol and was added and stirred until homogenous. 400 mL dH$_2$O containing 17 g KOH was added dropwise through the addition funnel, turning the yellow An ethylenically unsaturated, UV-absorbing monomer was prepared from the acid form of TINUVIN 213, as follows. A 500 mL, 3-neck round bottom flask equipped with a Freidrich condenser and stir bar was dried under vacuum and a heating gun for 10 minutes. 9.55 g (0.028 mol) of TINUVIN 213 acid (prepared above), 200 mL diethyl ether and 1.3 mL DMF was added to the round bottom. 2.75 mL (0.037 mol) thionyl chloride was slowly added to the mixture. The mixture stirred until homogenous (2-3 hours) except for a small amount of the Vilsmeier salt. 7 g of anhydrous Na$_2$CO$_3$ was added followed by slowly adding 18.33 g (0.141 mol) 2-hydroxyethyl methacrylate (HEMA). The reaction proceeded overnight and was monitored by TLC. Once the reaction proceeded to completion, the sodium carbonate was filtered off and the solution was added to a 1 L separatory funnel. 50 mL EtOAc and 100 mL hexane was added to the funnel. An organic wash was performed 5×300 mL with a 2% NaCl (aq) solution, discarding the aqueous phase. A 2×300 mL 5% Na$_2$CO$_3$ (aq) solution was then added, precipitating any remaining starting material. The precipitate was filtered off and the process was repeated until no precipitate was formed during the basic aqueous wash. A yellow, organic layer was thereby collected and dried over anhydrous Na$_2$SO$_4$, filtered and concentrated down by rotary evaporation. The yellow material was redissolved in a minimal amount of heptane and let sit overnight at room temperature to recrystallize. Recrystallization was further enhanced by placing the flask in a refrigerator for up to 48 hours, to form a methacrylated form of TINUVIN 213, with a yield of about 40%.

Example 16

Preparation of UV-Absorbing Polymer

A UV-absorbing polymer according to the invention was prepared as follows: 4.0 g TINUVIN 213 methacrylate as prepared in Example 15, 5.0 g Z-6030 silane (available from Dow Corning of Midland, Mich.), 1.0 g AIBN initiator and 65 mL ethyl acetate (EtOAc) were added to a 100 mL round bottom flask equipped with a Freidrich condenser and stir bar. The mixture was purged with nitrogen for 10 minutes then heated under reflux at 65° C. for 24 hours. The EtOAc was then distilled off by rotary evaporation and 4.2 g of CETIOL B (dibutyl adipate, available from Cognis Corporation of Monheim, Germany) was added to the round bottom yielding a 70 wt % of UV-absorbing polymer, 30 wt. % CETIOL B.

Example 17

Preparation of UV-Absorbing Polymer

A UV-absorbing polymer according to the invention was prepared in a manner identical to Example 16, except that 5.0 grams of lauryl methacrylate was substituted for Z-6030 silane, again yielding 70 wt. % of UV-absorbing polymer, 30 wt % CETIOL B.

Example 18

Preparation of UV-Absorbing Polymer

A UV-absorbing polymer according to the invention was prepared in a manner identical to Example 16, except that 5.0 grams of isooctyl acrylate was substituted for Z-6030 silane, again yielding 70 wt. % of UV-absorbing polymer, 30 wt % CETIOL B.

Example 19

Preparation of UV-Absorbing Monomer

An acid form of TINUVIN 109 (Ciba, Inc) was prepared, as follows. 21.21 g of TINUVIN 109 was added to a 1 liter, round bottom flask equipped with a stir bar and addition funnel. 300 mL of ethanol and was added and stirred until homogenous. 100 mL aqueous NaOH containing 10 mL of 50 wt % NaOH(aq) and 90 mL deionized water was added dropwise through the addition funnel, turning the yellow solution a dark, amber orange color. The reaction stirred for 24 hours and was monitored by TLC. After the reaction was complete about 200 mL of solvent was distilled off by rotary evaporation. 1N HCl (aq) was added, until a pH of 1 was achieved by litmus paper, precipitating a white precipitate. The white precipitate was filtered and washed with 1 N HCl (aq) 3×500 mL. It was then redissolved in 500 mL CHCl$_3$ and an organic extraction was performed with 2×300 mL 1 N HCl (aq). The organic layer was collected, dried over anhydrous Na$_2$SO$_4$, filtered, concentrated down by rotary evaporation and dried under vacuum overnight at 50° C., to form an acid form of TINUVIN 109, with a yield of about 90%.

An ethylenically unsaturated, UV-absorbing monomer was prepared from the acid form of TINUVIN 109, as follows. A 500 mL, 3-neck round bottom flask equipped with a Freidrich condenser and stir bar was dried under vacuum and a heating gun for 10 minutes. 6.78 g (0.020 mol) of TINUVIN 109 acid (prepared above), 150 mL diethyl ether and 3 mL DMF was added to the round bottom. 2.09 mL (0.0286 mol) thionyl chloride was slowly added to the mixture. The mixture stirred until homogenous (2-3 hours) except for a small amount of the Vilsmeier salt. 7 g of anhydrous Na$_2$CO$_3$ was added followed by slowly adding 7.8 g (0.06 mol) 2-hydroxyethyl methacrylate (HEMA). The reaction proceeded overnight and was monitored by TLC. Once the reaction proceeded to completion, the sodium carbonate was filtered off and the solution was added to a 1 L separatory funnel. 50 mL EtOAc and 100 mL hexane was added to the funnel. An organic wash was performed 5×300 mL with a 2% NaCl (aq) solution, discarding the aqueous phase. A 2×300 mL 5% Na$_2$CO$_3$ (aq) solution was then added, precipitating any remaining starting material. The precipitate was filtered off and the process was repeated until no precipitate was formed during the basic aqueous wash. A yellow, organic layer was thereby collected and dried over anhydrous Na$_2$SO$_4$, filtered and concentrated down by rotary evaporation. The yellow material was redissolved in a minimal amount of heptane and let sit overnight at room temperature to recrystallize. Recrystallization was further enhanced by placing the flask in a refrigerator for up to 48 hours, to form a methacrylated form of TINUVIN 109, with a yield of about 40% and a melting point of about 42° C.

Example 20

Preparation of UV-Absorbing Polymer

A UV-absorbing polymer according to the invention was prepared as follows: 4.0 g TINUVIN 109 methacrylate as prepared in Example 19, 5.0 g Z-6030 silane (available from Dow Corning of Midland, Mich.), 1.0 g AIBN initiator and 65 mL ethyl acetate (EtOAc) were added to a 100 mL round bottom flask equipped with a Freidrich condenser and stir bar. The mixture was purged with nitrogen for 10 minutes then heated under reflux at 65° C. for 24 hours. The EtOAc was then distilled off by rotary evaporation and 4.2 g of CETIOL B (dibutyl adipate, available from Cognis Corporation of Monheim, Germany) was added to the round bottom yielding a 70 wt % of UV-absorbing polymer, 30 wt. % CETIOL B. [40% TINUVIN 109, 50% silane, 10% initiator]

Example 21

Preparation of UV-Absorbing Polymer

A UV-absorbing polymer according to the invention was prepared in a manner identical to Example 20, except that 5.0 grams of lauryl methacrylate was substituted for Z-6030 silane, again yielding 70 wt. % of UV-absorbing polymer, 30 wt % CETIOL B.

Example 22

Preparation of UV-Absorbing Polymer

A UV-absorbing polymer according to the invention was prepared in a manner identical to Example 20, except that 5.0 grams of isooctyl acrylate was substituted for Z-6030 silane, again yielding 70 wt. % of UV-absorbing polymer, 30 wt % CETIOL B.

Example 23

UV-Absorbance—Comparison of UV-Absorbing Polymers Having Different UV-Absorbing Chromophores The UV-absorbing polymer of Example 20 and the UV-absorbing polymer of Example 6 were separately dissolved in CETIOL B, each to a concentration by weight of 20%. Since each of the polymers contained 40% UV-absorbing chromophore by weight, each sample contained 8% (20%×40%) by weight chromophore. The IN-VITRO SUN PROTECTION TEST METHOD was performed on both materials in order to compare the ability of each to absorb UV radiation. The results are shown in Table 10 below:

TABLE 10

| Polymer | % Polymer in CETIOL B | % Chromophore in Solution | SPF | PFA |
|---|---|---|---|---|
| Ex. 20 | 20 | 8 | 11.59 | 9.43 |
| Ex. 6 | 20 | 8 | 12.49 | 5.01 |

The results indicate that, when tested in CETIOL B, the polymer of Ex. 20, which included TINUVIN 109 as the UV-absorbing chromophore had superior UV-A absorbing properties as compared with the polymer of Ex. 6, which had NORBLOC as the UV-absorbing moiety. The ratio of PFA/SPF for the polymer of Ex. 20 was 0.89, whereas the PFA/SPF ratio for the polymer of Ex. 8 was only 0.40. This suggests that, by choosing the TINUVIN 109 as the UV-absorbing moiety, one can achieve even higher levels of UV-A protection. Furthermore, it suggests that by choosing the TINUVIN 109, one should be able to meet the desirable minimum ratio of PFA/SPF (0.33), yet still achieve a high SPF.

Example 24

A composition including a UV-absorbing polymer was prepared. The composition consisted of ingredients shown in Table 11 below:

TABLE 11

| Trade Name | INCI or CTFA Name | Percentage |
|---|---|---|
| Water | Water | 59.3 |
| Pemulen TR 1 | Acrylates/C10-30 alkyl acrylate crosspolymer | 0.2 |
| SPECTRAGARD | caprylyl glycol, hexylene glycol, methylisothiazolinone | 0.6 |
| ARLACEL 165 | Glyceryl Stearate, PEG-100 Stearate | 1.7 |
| AMPHISOL K | Potassium cetyl phosphate | 0.7 |
| Polymer of Example 20 | UV-absorbing polymer | 20.0 |
| CETIOL B | Dibutyl adipate | 6.0 |
| FINSOLV TN | C12-C15 alkyl benzoate | 3.0 |
| MYGLIOL 812 | Caprylic/capric triglycerides | 7.0 |
| LANETTE 16 | Cetyl alcohol | 0.5 |
| COSMEDIA ATH | Sodium Polyacrylate & Ethylhexyl Stearate & Trideceth-6 | 1.0 |
| Total | | 100 |

PEMULEN TR-1 is available from Noveon Inc. of Cleveland, Ohio
ARLACEL 165 is available from Uniqema Inc. of Chicago, Ill.
AMPHISOL K is available from DSM Nutritional Products of Parsippany, N.J.
CETIOL B and LANETTE 16 are available from Cognis Care Chemicals of Monheim, Germany
FINSOLV TN is available from Finetex Inc. of Elmwood Park, N.J.
MYGLIOL 812 is available from Sasol Germany GmbH of Witten, Germany
SPECTRAGARD is available from Inolex Chemical Company of Philadelphia, Pa.

The composition of Example 24 was made by first preparing a water phase by mixing water and PEMULEN and heating to 85 C. A small amount of sodium hydroxide was added to neutralize the PEMULEN to a pH of 5.5-6.0. An oil phase was then prepared by mixing the remainder of the ingredients (except the COSMEDIA ATH and SPECTRAGARD) together, adding it to the water phase, and homogenizing the two phases using a mixer set at 3500 rpm for 5 minutes. The COSMEDIA ATH was then slowly added and the mixture was allowed to cool to 30 C. SPECTRAGARD was then added, mixed gently, and allowed to cool to room temperature. The composition of Example 24 exhibited excellent spreadibility and aesthetics.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed:
1. A blend comprising:
  a first UV-absorbing polymer, said first UV-absorbing polymer comprising the polymerization reaction product of:
  a first ethylenically unsaturated monomer comprising a first pendant group that comprises a UV-absorbing moiety, and a second pendant group selected from the group consisting of H, or $C_1$ to $C_{12}$ alkyl; and
  a second ethylenically unsaturated monomer selected from the group consisting of monomethacryloxypropyl polydimethylsiloxane and methacryloxypropyl trimethoxysilane,
  wherein the number of repeat units of said first reacted monomer per molecule is from about 1 to about 6000 and the number of repeating units of said second reacted monomer per molecule is from about 2 to about 6300, said UV-absorbing polymer having a weight average molecular weight of at least 2000 and comprising at least 5 mole % of said first pendant group; and
  a second UV-absorbing polymer that comprises a UV-B absorbing moiety;
  wherein said blend is capable of providing both synergistic SPF and synergistic PFA protection over a mass percent range of the first and second UV-absorbing polymers of at least 40%.

2. The blend of claim 1, wherein said first UV-absorbing polymer comprises a carbon chain backbone and includes a UV-A absorbing moiety and said second UV-absorbing polymer comprises a siloxane backbone and includes a UV-B absorbing moiety.

3. The blend of claim 1, wherein said first UV-absorbing polymer has a weight average molecular weight of from about 2000 to about 1,000,000.

4. The blend of claim 1, wherein said second UV-absorbing polymer has a weight average molecular weight of at least 2000.

5. The blend of claim 1 further comprising a synergy promoting solvent.

6. The blend of claim 1 further comprising a benzoate ester.

7. The blend of claim 1, wherein the UV-A absorbing moiety comprises a UV-absorbing triazole.

8. The blend of claim 1, wherein the UV-B absorbing moiety comprises a benzylidene malonate silicone.

9. The blend of claim 1, further comprising a solvent system comprising a solvent having a dielectric constant from about 3 to about 8.

10. The blend of claim 1 wherein said second ethylenically unsaturated monomer comprises monomethacryloxypropyl polydimethylsiloxane.

11. The blend of claim 1 wherein said first ethylenically unsaturated monomer comprises 2-(2'hydroxy-5'-methacryloxyethylphenyl)-2H-benzotriazol and said second ethylenically unsaturated monomer comprises monomethacryloxypropyl polydimethylsiloxane.

\* \* \* \* \*